(12) United States Patent
Meyers

(10) Patent No.: US 10,223,505 B2
(45) Date of Patent: Mar. 5, 2019

(54) SECURED MEDICINES DISPENSING DEVICE

(71) Applicant: Mark Meyers, Camas, WA (US)

(72) Inventor: Mark Meyers, Camas, WA (US)

( * ) Notice: Subject to any disclaimer, the term of this patent is extended or adjusted under 35 U.S.C. 154(b) by 0 days.

(21) Appl. No.: 15/459,133

(22) Filed: Mar. 15, 2017

(65) Prior Publication Data

US 2018/0268111 A1    Sep. 20, 2018

(51) Int. Cl.
| | |
|---|---|
| *A61J 7/04* | (2006.01) |
| *G06F 19/00* | (2018.01) |
| *A61J 7/00* | (2006.01) |
| *B65D 43/16* | (2006.01) |
| *B65D 55/02* | (2006.01) |
| *B65D 51/24* | (2006.01) |
| *G06K 9/00* | (2006.01) |

(52) U.S. Cl.
CPC ........ *G06F 19/3462* (2013.01); *A61J 7/0084* (2013.01); *A61J 7/04* (2013.01); *A61J 7/0481* (2013.01); *B65D 43/163* (2013.01); *B65D 51/245* (2013.01); *B65D 55/02* (2013.01); *G06K 9/00013* (2013.01)

(58) Field of Classification Search
None
See application file for complete search history.

(56) References Cited

U.S. PATENT DOCUMENTS

| | | | | |
|---|---|---|---|---|
| 4,815,998 A * | 3/1989 | McGuire | ................. | A45C 1/12 109/61 |
| 5,221,024 A | 6/1993 | Campbell | | |
| 5,291,191 A * | 3/1994 | Moore | ................. | A61J 7/0084 221/3 |
| 6,415,202 B1 | 7/2002 | Halfacre | | |
| 6,529,446 B1 * | 3/2003 | de la Huerga | ........ | A61J 7/0084 368/10 |
| 7,359,765 B2 | 4/2008 | Varvarelis | | |
| 8,060,249 B2 * | 11/2011 | Bear | ..................... | A61J 7/0481 700/232 |
| 8,357,114 B2 * | 1/2013 | Poutiatine | ............. | A61J 7/0038 604/59 |
| D690,199 S | 9/2013 | Lee | | |
| 8,700,212 B1 * | 4/2014 | Bruno | ................... | A61J 7/0069 206/534 |

(Continued)

FOREIGN PATENT DOCUMENTS

WO    WO2011146664    11/2011

*Primary Examiner* — Timothy R Waggoner

(57) ABSTRACT

A secured medicines dispensing device for controlling access to medications includes a housing. A plurality of slats that is coupled to and extends between an annular wall of the housing to define a plurality of compartments. Each of a plurality of lids is positioned in a top of the housing and biased to an open configuration. A power module, a microprocessor and transmitter are coupled to the housing. A screen, which is touch-enabled, and a scanner configured to read a fingerprint of a user are coupled to the top of the housing. The microprocessor is operationally coupled to the power module. The transmitter, the screen, and the scanner are operationally coupled to the microprocessor. A plurality of locks is operationally coupled to the microprocessor. Each lock is coupled to a respective lid and selectively couplable to the housing to secure the lid in a closed configuration.

11 Claims, 3 Drawing Sheets

(56) References Cited

U.S. PATENT DOCUMENTS

| | | | |
|---|---|---|---|
| 2005/0209733 A1* | 9/2005 | Gilmore | A61G 12/001 700/231 |
| 2010/0314282 A1* | 12/2010 | Bowers | A61J 1/03 206/534 |
| 2014/0074283 A1 | 3/2014 | Blackburn | |
| 2014/0326744 A1 | 11/2014 | Ratnakar | |
| 2015/0148943 A1 | 5/2015 | Sullivan | |

* cited by examiner

SECURED MEDICINES DISPENSING DEVICE

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

(2) Description of Related Art Including Information Disclosed Under 37 CFR 1.97 and 1.98

The disclosure and prior art relates to medicines dispensing devices and more particularly pertains to a new medicines dispensing device for controlling access to medications.

BRIEF SUMMARY OF THE INVENTION

An embodiment of the disclosure meets the needs presented above by generally comprising a housing. A plurality of slats that is coupled to and extends between an annular wall of the housing to define a plurality of compartments. Each of a plurality of lids is positioned in a top of the housing and biased to an open configuration. A power module, a microprocessor and transmitter are coupled to the housing. A screen, which is touch-enabled, and a scanner configured to read a fingerprint of a user are coupled to the top of the housing. The microprocessor is operationally coupled to the power module. The transmitter, the screen, and the scanner are operationally coupled to the microprocessor. A plurality of locks is operationally coupled to the microprocessor. Each lock is coupled to a respective lid and selectively couplable to the housing to secure the lid in a closed configuration. The screen is configured to enter commands into the microprocessor to define a dosing regimen. The microprocessor is positioned to compel the lock to decouple from the housing so that the lid is compelled to the open configuration. The lid is configured to access the one or more medications that are positioned in the respective compartment according to the dosing regimen. The scanner is configured to authenticate the user to access a respective compartment at a specified time based on the dosing regimen. The microprocessor is positioned to compel the transmitter to notify a responsible party in event of improper handling of the housing and attempted unauthorized accessing of medicines that are positioned in the compartments.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
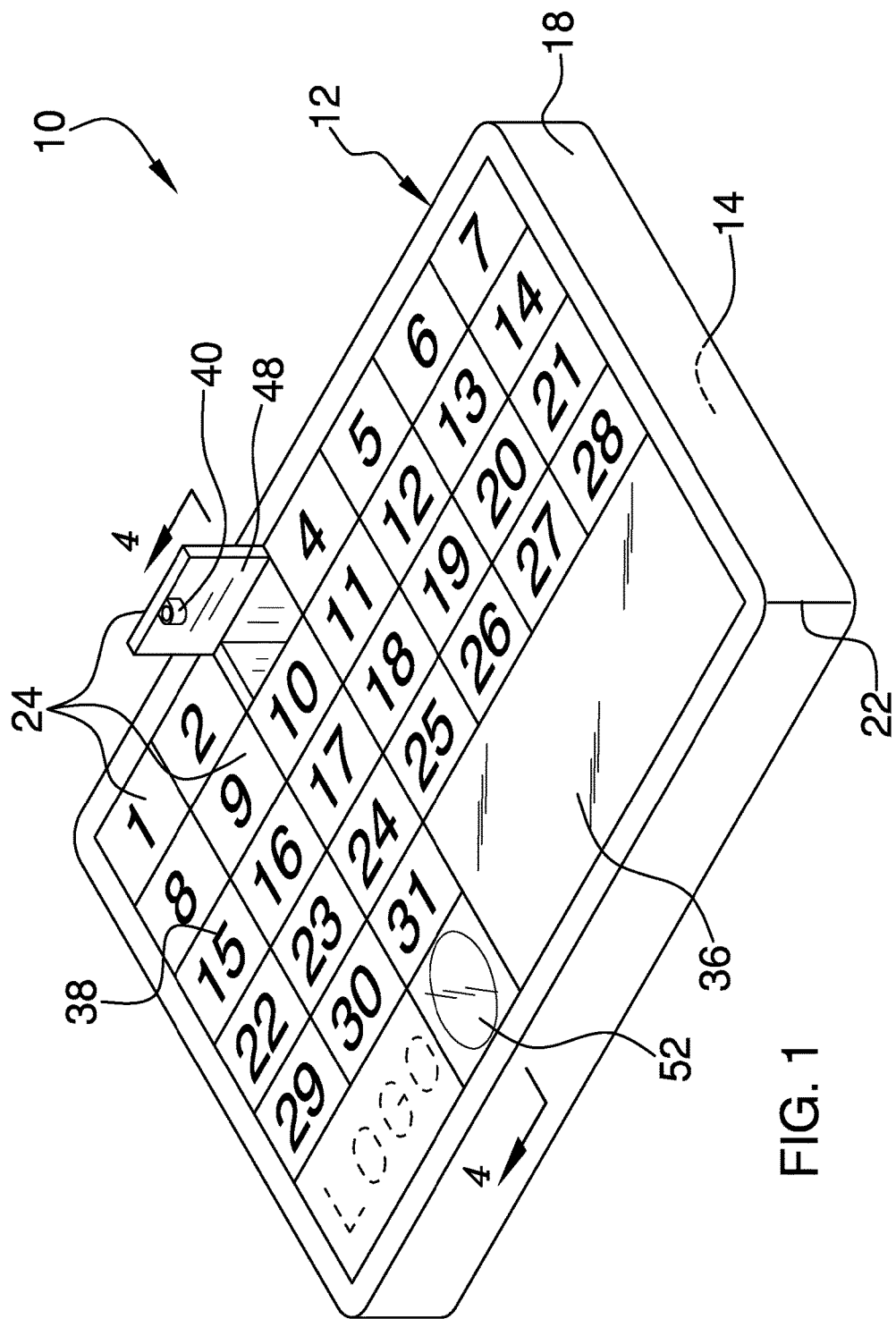
FIG. 1 is an isometric perspective view of a secured medicines dispensing device according to an embodiment of the disclosure.
Figure 2:
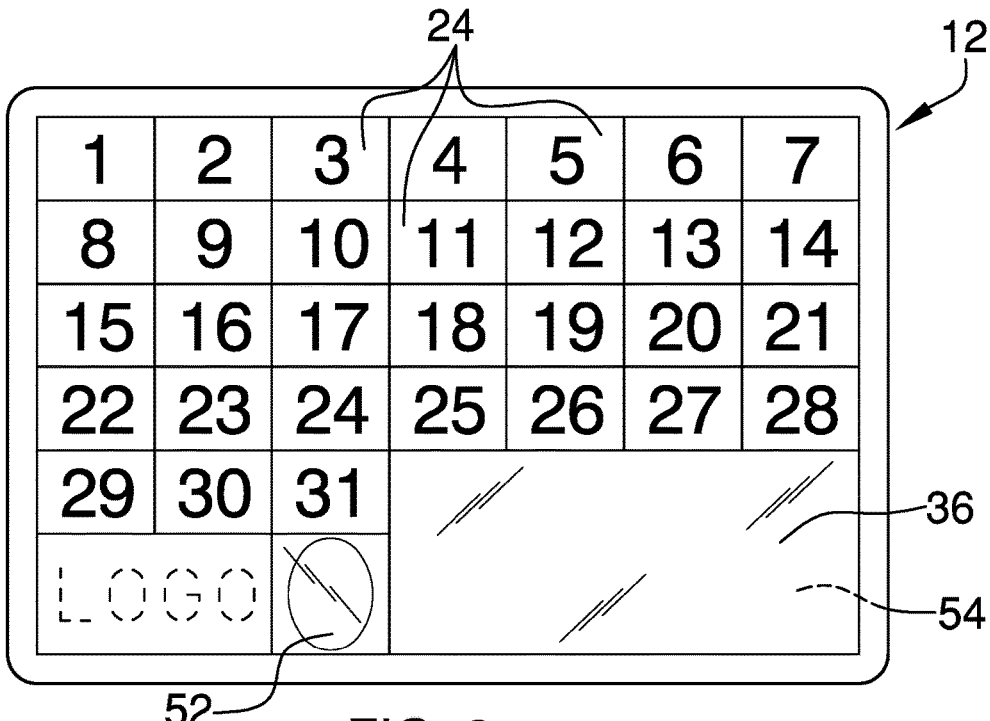
FIG. 2 is a top view of an embodiment of the disclosure.
Figure 3:
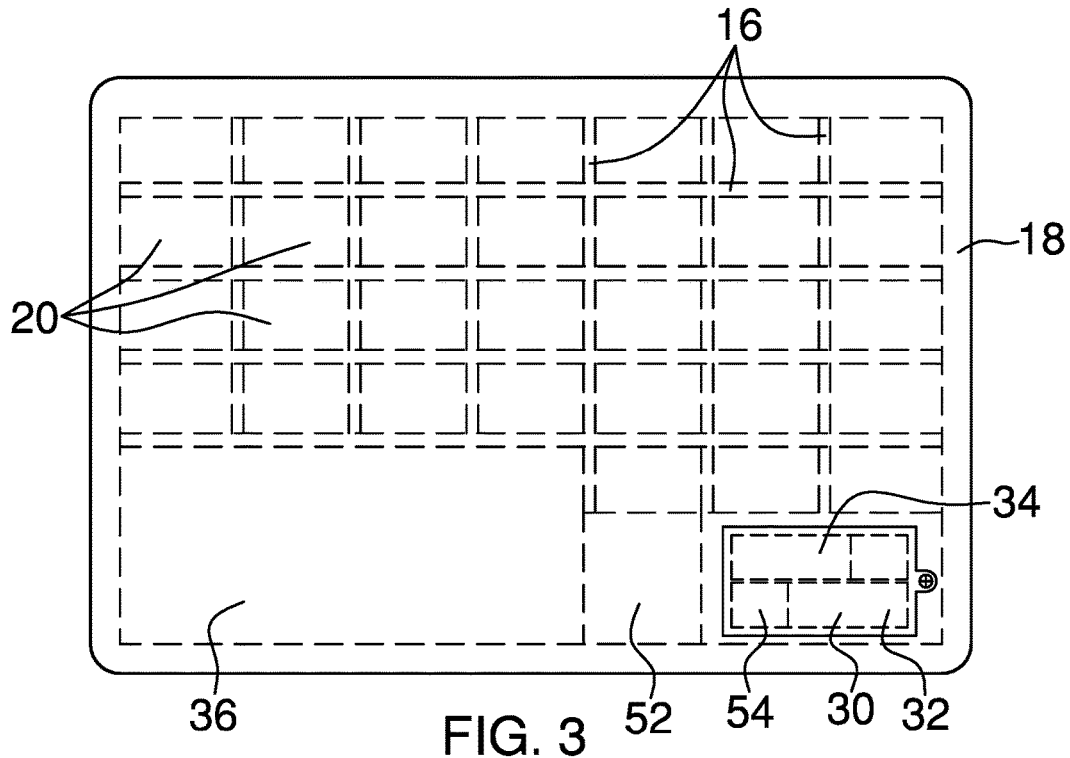
FIG. 3 is a cross-sectional view of an embodiment of the disclosure.
Figure 4:
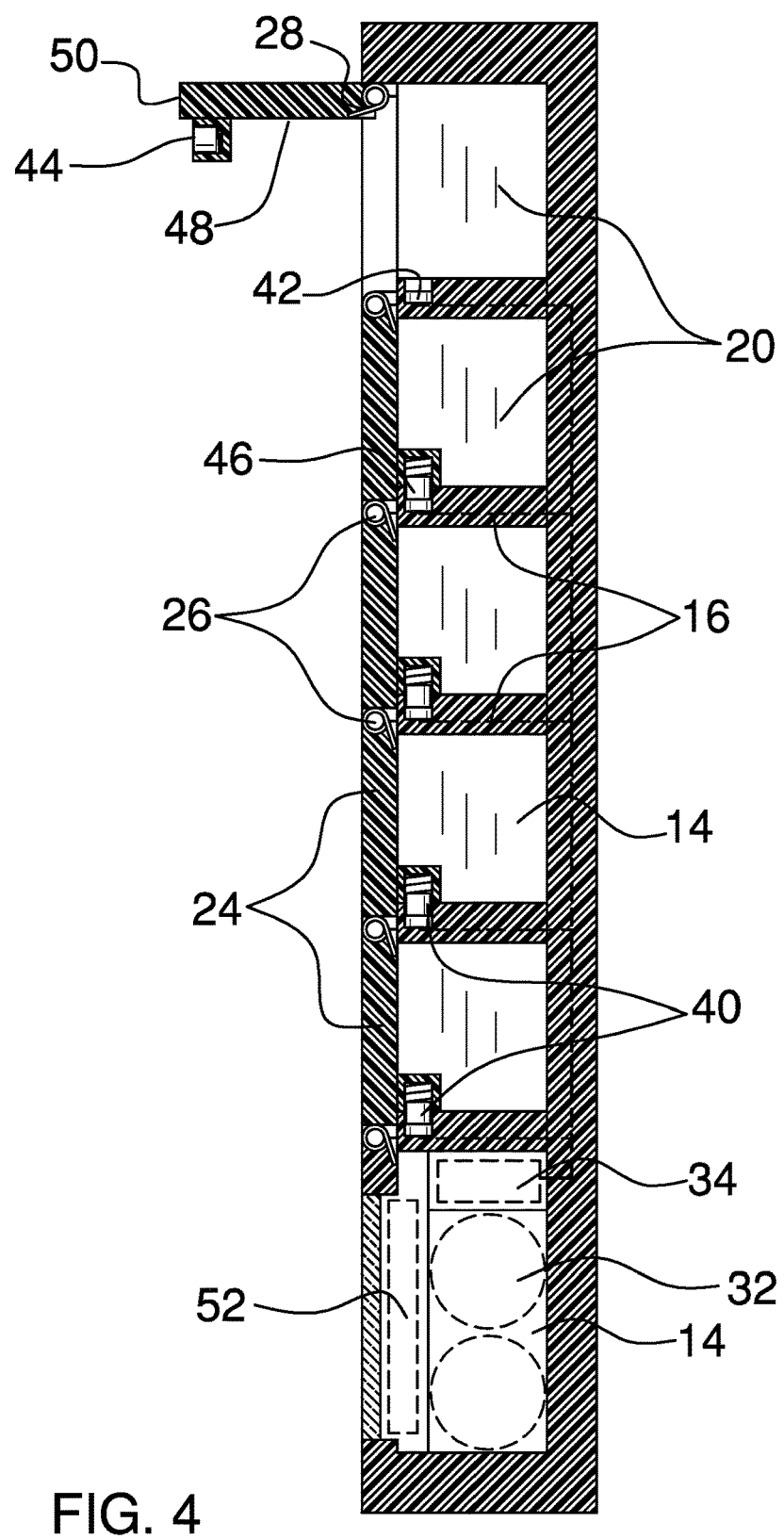
FIG. 4 is a cross-sectional view of an embodiment of the disclosure.

With reference now to the drawings, and in particular to FIGS. 1 through 4 thereof, a new medicines dispensing device embodying the principles and concepts of an embodiment of the disclosure and generally designated by the reference numeral 10 will be described.

As best illustrated in FIGS. 1 through 4, the secured medicines dispensing device 10 generally comprises a housing 12 that defines an internal space 14. The housing 12 comprises a plurality of slats 16 that is coupled to and extends between an annular wall 18 of the housing 12 to define a plurality of compartments 20. In one embodiment, the plurality of slats 16 is positioned to define thirty-one compartments 20. In another embodiment, the housing 12 is substantially rectangularly box shaped. The housing 12 has corners 22. In yet another embodiment, the corners 22 are rounded. In still yet another embodiment, the housing 12 comprises plastic. In still yet another embodiment, the housing 12 comprises metal.

A plurality of lids 24 is positioned in a top 38 of the housing 12. Each lid 24 is biased to an open configuration. The lid 24 is positioned to allow access to one or more medications that are positioned in a respective compartment 20. In one embodiment, each lid 24 is numbered to indicate a respective day of a month. Each of a plurality of hinges 26 is coupled to a first end 28 of a respective lid 24. The hinges 26 are spring-loaded so that the lids 24 are biased to the open configuration.

A power module 30 is coupled to the housing 12 and is positioned in the internal space 14. In one embodiment, the power module 30 comprises at least one battery 32. A microprocessor 34 is coupled to the housing 12 and is positioned in the internal space 14. The microprocessor 34 is operationally coupled to the power module 30. A screen 36 is coupled to the top 38 of the housing 12. The screen 36 is operationally coupled to the microprocessor 34. The screen 36 is touch-enabled. The screen 36 is configured to allow entry into the microprocessor 34 of commands for a dosing regimen.

A plurality of locks 40 is operationally coupled to the microprocessor 34. Each lock 40 is coupled to a respective lid 24 and is selectively couplable to the housing 12. The lock 40 is positioned to couple to the housing 12 to secure the lid 24 in a closed configuration. The microprocessor 34 is positioned to compel the lock 40 to decouple from the housing 12 so that the lid 24 is compelled to the open configuration. The lid 24 is configured to allow access to the one or more medications that are positioned in the respective compartment 20 according to the dosing regimen.

The screen 36 is enabled to allow entry into the microprocessor 34 of an override command so that an authorized person, such as a pharmacist and nurse, can compel the microprocessor 34 to compel the locks 40 to decouple from the housing 12. The lids 24 are compelled to the open configuration and the compartments 20 are configured to position the one or more medications in the compartments 20.

Each lock 40 comprises an electromagnet 42 and a piston 44. The electromagnet 42 is coupled to a respective slat 16 and is positioned in a recess 46 that is positioned in the respective slat 16. The piston 44 is springedly coupled to an underside 48 of the lid 24 of the respective compartment 20 proximate to a second end 50 of the lid 24. The piston 44 is biased to a retracted position. The electromagnet 42 is positioned to magnetically couple to the piston 44 to position the piston 44 in the recess 46 to couple the lid 24 to the housing 12. The microprocessor 34 is positioned to compel the electromagnet 42 to demagnetize so that the piston 44 is retracted from the recess 46. The hinge 26 is positioned to compel the lid 24 to the open configuration. The lid 24 is configured to allow access to the one or more medications that are positioned in the respective compartment 20 according to the dosing regimen.

A scanner 52 is coupled to the top 38 of the housing 12. The scanner 52 is operationally coupled to the microprocessor 34. The scanner 52 is configured to read a fingerprint of a user. The scanner 52 is configured to authenticate the user to allow access to a respective compartment 20 at a specified time based on the dosing regimen.

A transmitter 54 is coupled to the housing 12 and is positioned in the internal space 14. The transmitter 54 is operationally coupled to the microprocessor 34. The microprocessor 34 is positioned to compel the transmitter 54 to notify a responsible party in event of improper handling of the housing 12 and attempted unauthorized accessing of medicines that are positioned in the compartments 20. The microprocessor 34 also is configured to compel the transmitter 54 to transmit a notification to an electronic device, such as a cellular phone of the user, to access a respective compartment 20 at the specified time based on the dosing regimen. The user is reminded to medicate.

In use, the screen 36 is configured to enter the override command into the microprocessor 34. The authorized person, such as the pharmacist and the nurse, can compel the microprocessor 34 to compel the locks 40 to decouple from the housing 12. The lids 24 are compelled to the open configuration and the compartments 20 are configured to position the one or more medications in the compartments 20. The screen 36 is configured to enter the commands for the dosing regimen into the microprocessor 34. The electromagnet 42 is positioned in the recess 46 such that electromagnet 42 is positioned to magnetically couple to the piston 44. The piston 44 is positioned in the recess 46 to couple the lid 24 to the housing 12. The microprocessor 34 is positioned to compel the electromagnet 42 to demagnetize so that the piston 44 is retracted from the recess 46. The hinge 26 is positioned to compel the lid 24 to the open configuration. The lid 24 is configured to allow access to the one or more medications that are positioned in the respective compartment 20 according to the dosing regimen. The scanner 52 is configured to authenticate the user to allow access to the respective compartment 20 at the specified time based on the dosing regimen. The microprocessor 34 is positioned to compel the transmitter 54 to notify the responsible party in the event of improper handling of the housing 12 and the attempted unauthorized accessing of the medicines that are positioned in the compartments 20. The microprocessor 34 also is configured to compel the transmitter 54 to transmit a notification to the electronic device, such as the cellular phone of the user, to access the respective compartment 20 at the specified time based on the dosing regimen. The user is reminded to medicate.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A secure medicines dispensing device comprising:
   a housing defining an internal space, said housing comprising a plurality of slats coupled to and extending between an annular wall of said housing defining a plurality of compartments;
   a plurality of lids positioned in a top of said housing, each said lid of said plurality of lids being biased to an open configuration such that each said lid of said plurality of lids is positioned for accessing one or more medications positioned in a respective said compartment;
   a power module coupled to said housing and positioned in said internal space;
   a microprocessor coupled to said housing and positioned in said internal space, said microprocessor being operationally coupled to said power module;

a screen coupled to said top of said housing, said screen being operationally coupled to said microprocessor, said screen being touch-enabled;

a plurality of locks operationally coupled to said microprocessor, each said lock of said plurality of locks being coupled to a respective said lid of said plurality of lids and selectively couplable to said housing;

a scanner coupled to said top of said housing, said scanner being operationally coupled to said microprocessor, said scanner being configured for reading a fingerprint of a user;

a transmitter coupled to said housing and positioned in said internal space, said transmitter being operationally coupled to said microprocessor;

wherein said screen is positioned on said housing such that said screen is configured for entering commands for a dosing regimen into said microprocessor, wherein each said lock of said plurality of locks is positioned on said respective said lid of said plurality of lids such that said lock of said plurality of locks is positioned for coupling to said housing for securing said respective said lid of said plurality of lids in a closed configuration, and wherein said microprocessor is positioned for compelling each said lock of said plurality of locks to decouple from said housing such that said respective said lid of said plurality of lids is compelled to the open configuration such that said respective said lid of said plurality of lids is configured for accessing the one or more medications positioned in said respective said compartment according to the dosing regimen, wherein said scanner is positioned on said housing such that said scanner is configured for authenticating the user for accessing a respective said compartment at a specified time based on the dosing regimen, wherein said transmitter is positioned in said housing such that said microprocessor is positioned for compelling said transmitter for notifying a responsible party in event of improper handling of said housing and attempted unauthorized accessing of medicines positioned in said compartments;

a plurality of hinges, each said hinge of said plurality of hinges being coupled to a first end of a respective said lid of said plurality of lids, each of said hinges of said plurality of hinges being spring-loaded such that said plurality of lids is biased to the open configuration; and wherein each said lock comprises
an electromagnet, said electromagnet being coupled to a respective said slat and positioned in a recess positioned in said respective said slat;
a piston said piston being springedly coupled to an underside of said respective said lid of said respective said compartment proximate to a second end of said respective said lid, said piston being biased to a retracted position; and
wherein said electromagnet is positioned in said recess such that electromagnet is positioned for magnetically coupling to said piston for positioning said piston in said recess to couple said lid to said housing, and wherein said microprocessor is positioned for compelling said electromagnet to demagnetize such that said piston is retracted from said recess such that said hinge is positioned for compelling said respective said lid to the open configuration such that said respective said lid is configured for accessing the one or more medications positioned in said respective said compartment according to the dosing regimen.

2. The device of claim 1, further including said housing being substantially rectangularly box shaped.

3. The device of claim 1, further including said plurality of slats being positioned to define thirty-one said compartments.

4. The device of claim 1, further including said housing having corners, said corners being rounded.

5. The device of claim 1, further including said housing comprising plastic.

6. The device of claim 1, further including said housing comprising metal.

7. The device of claim 3, further including each said lid being numbered for indicating a respective day of a month.

8. The device of claim 1, further including said power module comprising at least one battery.

9. The device of claim 1, further including said screen being enabled for entering an override command into said microprocessor such that an authorized person, such as a pharmacist and nurse, can compel said microprocessor to compel said locks to decouple from said housing such that said lids are compelled to the open configuration, such that said compartments are configured for positioning the one or more medications in said compartments.

10. The device of claim 1, further including said microprocessor being configured for compelling said transmitter to transmit a notification for accessing a respective said compartment at the specified time based on the dosing regimen to an electronic device, such as a cellular phone, of the user, such that the user is reminded to medicate.

11. A secured medicines dispensing device comprising:
a housing defining an internal space, said housing comprising a plurality of slats coupled to and extending between an annular wall of said housing defining a plurality of compartments, said housing being substantially rectangularly box shaped, said plurality of slats being positioned to define thirty-one said compartments, said housing having corners, said corners being rounded, said housing comprising plastic, said housing comprising metal;
a plurality of lids positioned in a top of said housing, each said lid of said plurality of lids being biased to an open configuration such that each said lid of said plurality of lids is positioned for accessing one or more medications positioned in a respective said compartment, each said lid of said plurality of lids being numbered for indicating a respective day of a month;
a plurality of hinges, each said hinge of said plurality of hinges being coupled to a first end of a respective said lid of said plurality of lids, said plurality hinges being spring-loaded such that said plurality of lids is biased to the open configuration;
a power module coupled to said housing and positioned in said internal space, said power module comprising at least one battery;
a microprocessor coupled to said housing and positioned in said internal space, said microprocessor being operationally coupled to said power module;
a screen coupled to said top of said housing, said screen being operationally coupled to said microprocessor, said screen being touch-enabled, wherein said screen is positioned on said housing such that said screen is configured for entering commands for a dosing regimen into said microprocessor;
a plurality of locks operationally coupled to said microprocessor, each said lock of said plurality of locks being coupled to a respective said lid of said plurality of lids and selectively couplable to said housing, wherein each said lock of said plurality of locks is positioned on said respective said lid of said plurality of lids such that said lock of said plurality of locks is positioned for coupling to said housing for securing said respective said lid of said plurality of lids in a closed configuration and wherein said microprocessor is positioned for compelling each said lock of said plurality of locks to decouple from said housing such that said respective said lid of said plurality of lids is compelled to the open configuration such that said respective said lid of said plurality of lids is configured for accessing the one or more medications positioned in said respective said compartment according to the dosing regimen, said screen being enabled for entering an override command into said microprocessor such that an authorized person, such as a pharmacist and nurse, can compel said microprocessor to compel said plurality of locks to decouple from said housing such that said plurality of lids is compelled to the open configuration, such that said compartments are configured for positioning the one or more medications in said compartments, each said lock of said plurality of locks comprising an electromagnet, and a piston, said electromagnet being coupled to a respective said slat and positioned in a recess positioned in said respective said slat, said piston being springedly coupled to an underside of said respective said lid of said respective said compartment proximate to a second end of said respective said lid, said piston being biased to a retracted position, wherein said electromagnet is positioned in said recess such that electromagnet is positioned for magnetically coupling to said piston for positioning said piston in said recess to couple said respective said lid to said housing, and wherein said microprocessor is positioned for compelling said electromagnet to demagnetize such that said piston is retracted from said recess such that said hinge is positioned for compelling said respective said lid to the open configuration such that said respective said lid is configured for accessing the one or more medications positioned in said respective said compartment according to the dosing regimen;

a scanner coupled to said top of said housing, said scanner being operationally coupled to said microprocessor, said scanner being configured for reading a fingerprint of a user, wherein said scanner is positioned on said housing such that said scanner is configured for authenticating the user for accessing a respective said compartment at a specified time based on the dosing regimen;

a transmitter coupled to said housing and positioned in said internal space, said transmitter being operationally coupled to said microprocessor, wherein said transmitter is positioned in said housing such that said microprocessor is positioned for compelling said transmitter for notifying a responsible party in event of improper handling of said housing and attempted unauthorized accessing of medicines positioned in said compartments, said microprocessor being configured for compelling said transmitter to transmit a notification for accessing a respective said compartment at the specified time based on the dosing regimen to an electronic device, such as a cellular phone, of the user, such that the user is reminded to medicate; and wherein said screen is positioned on said housing such that said screen is configured for entering the override command into said microprocessor such that the authorized person, such as the pharmacist and the nurse, can compel said microprocessor to compel said plurality of locks to decouple from said housing such that said plurality of lids is compelled to the open configuration, such that said compartments are configured for positioning the one or more medications in said compartments, wherein said screen is configured for entering the commands for the dosing regimen into said microprocessor, wherein said electromagnet is positioned in said recess such that electromagnet is positioned for magnetically coupling to said piston for positioning said piston in said recess to couple said lid to said housing, wherein said microprocessor is positioned for compelling said electromagnet to demagnetize such that said piston is retracted from said recess such that said hinge is positioned for compelling said lid to the open configuration such that said lid is configured for accessing the one or more medications positioned in said respective said compartment according to the dosing regimen, wherein said scanner is positioned on said housing such that said scanner is configured for authenticating the user for accessing said respective said compartment at the specified time based on the dosing regimen, wherein said transmitter is positioned in said housing such that said microprocessor is positioned for compelling said transmitter for notifying the responsible party in the event of improper handling of said housing and the attempted unauthorized accessing of the medicines positioned in said compartments, and wherein said microprocessor is configured for compelling said transmitter to transmit a notification for accessing said respective said compartment at the specified time based on the dosing regimen to the electronic device, such as the cellular phone, of the user, such that the user is reminded to medicate.

\* \* \* \* \*